(12) United States Patent
Vestweber

(10) Patent No.: US 11,259,811 B2
(45) Date of Patent: Mar. 1, 2022

(54) ANASTOMOTIC DEVICE

(71) Applicant: Covidien LP, Mansfield, MA (US)

(72) Inventor: Boris Vestweber, Cologne (DE)

(73) Assignee: Covidien LP, Mansfield, MA (US)

( * ) Notice: Subject to any disclaimer, the term of this patent is extended or adjusted under 35 U.S.C. 154(b) by 205 days.

(21) Appl. No.: 16/600,686

(22) Filed: Oct. 14, 2019

(65) Prior Publication Data

US 2020/0038028 A1 Feb. 6, 2020

Related U.S. Application Data

(63) Continuation of application No. 14/117,206, filed as application No. PCT/EP2011/003609 on Jul. 19, 2011, now Pat. No. 10,441,288.

(30) Foreign Application Priority Data

May 20, 2011 (DE) .............................. 102011102686

(51) Int. Cl.
*A61B 17/064* (2006.01)
*A61B 17/115* (2006.01)
(Continued)

(52) U.S. Cl.
CPC ......... *A61B 17/115* (2013.01); *A61B 17/1114* (2013.01); *A61B 17/1155* (2013.01);
(Continued)

(58) Field of Classification Search
CPC ... A61B 17/007; A61B 17/115; A61B 17/068; A61B 17/00557
See application file for complete search history.

(56) References Cited

U.S. PATENT DOCUMENTS

| | | | |
|---|---|---|---|
| 5,487,499 A | | 1/1996 | Sorrentino et al. |
| 5,533,661 A | * | 7/1996 | Main .................... A61B 17/115 |
| | | | 227/176.1 |

(Continued)

FOREIGN PATENT DOCUMENTS

EP 1754445 A2 2/2007

OTHER PUBLICATIONS

International Search Report for PCT/EP2011/003609 dated Mar. 13, 2012 (4 pages).

*Primary Examiner* — Eyamindae C Jallow
(74) *Attorney, Agent, or Firm* — Carter, DeLuca & Farrell LLP

(57) ABSTRACT

Illustrated and described is an anastomotic device for forming anastomoses, in particular of intestine anastomoses, with an introducer sheath for insertion into a body lumen, wherein a thrust bearing part is provided for the head section and within the head section an extendable and retractable knife and a retaining pin are arranged. According to the invention at least the actuating part and the head section of inter-connected fluid supply channel and at the head section at least one fluid outlet connected with the fluid supply channel are provided for producing a fluidic connection between the actuating part and the head section while inserting the head section into the body lumen and/or when pushing the introducer sheath into the body lumen, in which the fluidic connection is configured for discharging an inflation liquid into the body lumen.

16 Claims, 3 Drawing Sheets

(51) Int. Cl.
   *A61B 17/11* (2006.01)
   *A61B 90/00* (2016.01)
   *A61B 17/072* (2006.01)

(52) U.S. Cl.
   CPC ............. *A61B 2017/07257* (2013.01); *A61B 2017/07285* (2013.01); *A61B 2090/08021* (2016.02); *A61B 2217/007* (2013.01)

(56) References Cited

U.S. PATENT DOCUMENTS

| | | | |
|---|---|---|---|
| 6,451,029 B1 | 9/2002 | Yeatman | |
| 7,757,924 B2 | 7/2010 | Gerbi et al. | |
| 7,922,743 B2* | 4/2011 | Heinrich | A61B 17/00491 606/219 |
| 8,181,838 B2 | 5/2012 | Milliman et al. | |
| 8,864,009 B2* | 10/2014 | Shelton, IV | A61B 17/00491 227/175.1 |
| 10,441,288 B2 | 10/2019 | Vestweber | |
| 2002/0115989 A1* | 8/2002 | Abboud | A61B 18/02 606/20 |
| 2003/0183671 A1 | 10/2003 | Mooradian et al. | |
| 2006/0108393 A1 | 5/2006 | Heinrich et al. | |
| 2007/0244492 A1 | 10/2007 | Suh | |
| 2010/0163598 A1* | 7/2010 | Belzer | A61B 17/115 227/181.1 |
| 2010/0230467 A1 | 9/2010 | Criscuolo et al. | |
| 2010/0320252 A1 | 12/2010 | Viola et al. | |
| 2016/0128695 A1 | 5/2016 | Vestweber | |
| 2016/0143641 A1* | 5/2016 | Sapienza | A61B 17/068 227/175.1 |

* cited by examiner

ANASTOMOTIC DEVICE

CROSS-REFERENCE TO RELATED APPLICATIONS

This application is a continuation application of U.S. application Ser. No. 14/117,206, filed Nov. 7, 2014, now U.S. Pat. No. 10,441,288, which is a national filing of International Application Serial No. PCT/EP2011/003609, filed Jul. 19, 2011, which claims the benefit of German Patent Application Serial no. 10 2011 102 686.3, filed May 20, 2011, the disclosure of each of which is hereby incorporated by reference herein.

BACKGROUND

Technical Field

The present disclosure relates to surgical fastener inserter instruments, and more particularly to surgical fastener inserter instruments for joining tubular sections of tissue such as intestinal anastomoses.

Background of Related Art

The present disclosure relates to anastomotic devices for the formation of anastomoses and, in particular, to intestinal anastomoses. In surgery, operationally produced connections between blood vessels, nerves and hollow organs, like, for example, sections of the large intestines, are designated as anastomoses. Fundamentally, the anastomosis is understood as a connection between two anatomical structures. For producing anastomoses, anastomotic devices of different design can be used, in particular the so called fastener inserters or clamp inserters. While carrying out surgical clamping operation with such a clamp inserter, two tissue parts and/or areas are interconnected by a set of clips, which form a body lumen in each case, such as, for example, two separate large intestine parts.

DE application no. 10 2007 057 207 A1 discloses a surgical clamp inserter for forming anastomoses, which ejects the clamps from a head section and brings them into an anvil section. The head section has a hollow-cylindrical head section facing the anvil section, and an retractable and extendable knife is arranged in the head section. The head section takes up a clamp device. Within an area surrounded by the head section, a retractable and extendable retaining pin or trocar tip is arranged, with which the anvil section is connected. The anvil section is provided with an arrangement of clamp shaping recesses, wherein the clamps are driven into the tissue and the clamps at the anvil section are formed or remodeled by manipulating the clamp device. For the formation of an intestinal anastomosis, a section of the intestine having a pathological tissue is removed in the first step. The intestine is divided into a first section with a proximal end and a second section area with a distal end, whereby the sections must be joined by a link again, in order to reproduce the continence. This connection with clamp inserter is known from DE application no. 10 2007 057 207 A1. The anvil section has a thrust bearing part, which is removed from the head section and inserted with a so-called purse-string suture into the proximal end of the first section of the intestine. The open end of the distal end of the second section is sutured with a cross suture. Subsequently, the head section of the anastomotic device (without the anvil section) is introduced through the anus and then up to the sealed end of the second section of the intestine. Afterwards the cross suture of the second section is punctured by the retaining pin of the head section, and the retaining pin forms a positive connection with the thrust bearing part of the anvil section. The retaining pin is now telescoped into the head section with the coupled thrust bearing part, which is located in the first section of the intestine, so that the sections of tissue are clamped together. The thrust bearing part is moved against the head section, so that a clamping and the subsequent separation of the surplus tissue can be accomplished. After re-establishing the continence, the anastomotic device is retracted completely from the body lumen and removed from the anus.

Well-known anastomotic devices have the disadvantage that the surrounding body tissue often gets damaged during insertion into the body lumen and thus leads to pain after the operation. This occurs in particular with such anastomotic devices, which have a sharp edged head-section and enlarged in the distal direction. The forward movement of the head section within the body lumen, in particular with heavily lined intestinal mucosa, is then clearly affected and the operational risk increased.

In order to effectively avoid injury to the body, in particular to the anal canal, while inserting the head section of clamp inserter, as known from DE application no. 10 2007 057 207 A1, into the body of the patient, in case of the known clamp inserter a provision is made such that in the anvil section removed by the trocar tip the front end of the head section can be covered by a cap. The cap is attached to the trocar tip. The trocar tip is extended such that with attached cap the cap covers the front end of the head section, thus fitting the same. Therefore, the cap covers at least those front areas of the head section, which are relatively sharp edged and can lead to injuries while inserting the head section through the anal canal. While inserting the equipment, the cap executes thus the function of a protective cap. Using the cap, a thread arranged outside of the device is connected, wherein for removing the cap the trocar tip is inserted, so that the trocar tip is disengaged with the cap. The cap can be taken off the head section without laterally touching at the head section by means of the thread present on the cap and remains laterally apart from the head section. After the clamping process and/or connecting the two intestine ends, the clamp inserter is pulled through the anal canal out of the body of the patient. The cap is pulled out by means of the thread through the anal canal. In the case of known clamp inserter, it is disadvantageous that the cap is taken off via a thread from the head section and afterwards remains by the side of the head section. When taking out the thread and by arranging the cap beside the head section it can cause injuries to the surrounding tissue in case of movement of the head section. In all other respects, it can be seen that taking off the cap with the thread is not easily possible, if the head section on the side of the thread lies close against the tissue. Even pulling the cap out of a body lumen with the help of the thread is difficult and can lead to further injuries of the body tissue.

There is a need to make available an anastomotic device of the kind described earlier, which would allow easy insertion into a body lumen and with a less danger of injuries to the surrounding body tissue. Further, the said anastomotic device should allow a leak test before by surgery of a sealed, in particular, the sutured opening of the body lumen, such as, for example, the leak test of a cross suture in a distal portion of the large intestine.

SUMMARY

The disclosure relates to anastomotic device for the formation of anastomoses, in particular intestinal anastomoses, with an introducer sheath for feeding into a body lumen, preferably into the large intestine, with a particularly thickened or swelled head section at the distal end of the introducer sheath and with an actuating part at the proximal end of the introducer sheath. The anastomotic device has an anvil section with a thrust bearing part, and a retractable and extendable knife and a retaining pin arranged within the head section. The thrust bearing part can be moved relative to the head section. The retaining pin can be joined to the thrust bearing part of the anvil section. The thrust bearing part can be moved by moving the retaining pin into the head section.

In order to avoid injuries to the intestinal tissue while inserting the anastomotic device, an isotonic saline solution or even water in the introducer sheath can rinse the intestine via the sphincter muscle. If the liquid is transported into the intestine passing the device on the side of the device, this is again retracted into the device while pushing then anastomotic device and is pressed out of the piece of the intestine.

In the case of an anastomotic device of the type as specified above, an inter-connected fluid supply channel extends to the head section and has at least a fluid outlet are provided for producing a fluidic connection between the actuating part and the head section while inserting of the head section into the body lumen and/or when pushing the introducer sheath forward in the body lumen. The fluidic connection is configured for discharging an inflation liquid into the body lumen. In a preferred manner, the fluid supply channel is extended on the basis of the actuating part inside the introducer sheath up to the head section.

To simplify the insertion of the head section in the body lumen and pushing the introducer sheath forward into the body lumen, the body lumen and/or the body tissue restricting the body lumen are inflated and, in doing so, injuries to the surrounding body tissue, as they occur when pushing the sharp-edged head section forward in the anastomotic devices as known from prior art, can be effectively avoided. Thanks to the filling of the body lumen with the inflation liquid, the insertion and pushing forward of the said anastomotic device is facilitated with small frictional resistance. In particular, the said anastomotic device is suitable for the formation of an anastomosis between two (large) intestine parts with heavily lined intestinal mucosa. Filling the intestine with the inflation liquid improves the sliding ability of the anastomotic device in the piece of intestine, wherein it is possible in a simple way to push the anastomotic device forward to a specific point in the intestine.

The body lumen is inflated by adding an inflation liquid through the introducer sheath and the head section of the said anastomotic device and/or if necessary, by the retaining pin, in certain embodiments. During insertion in the head section and/or while pushing the introducer sheath of the anastomotic device forward into the body lumen and, preferably, with an anastomotic device configured like a clamp inserter before puncturing a surgically sealed, in particular sutured, opening of the body lumen, the liquid supply is provided with the retaining pin of the anastomotic device. In particular, the fluid addition takes place before puncturing the suture and before connecting the thrust bearing part with the head section. The term "suture" is used here in a very general sense. According to the invention, a suture can be obtained by sewing, clamping, sticking or joining of an opening of the body lumen together. Deflating the lumen can take place automatically when pulling the anastomotic device out of the body lumen. In principle, it is also possible that inflation liquid can be sucked off through at least one outlet in the head section and the introducer sheath from the body lumen.

Further, the leak-tightness of a distal portion of the intestine sealed with a cross suture can be checked by Inflating in a simple way. In order to check the leak-tightness of a suture, a liquid with a dye can be supplied as inflation liquid, preferably water or isotonic saline solution, wherein using a simple visual control it can be determined whether and to what extent the supplied inflation liquid comes out through the suture from the body lumen. Besides, the inflation degree of the body lumen and/or volume increase can be visually checked while inflating and "overfilling" can be safely avoided. The addition of inflation liquid into the body lumen fulfils thus a dual function. Preferably a wound-treatment inert liquid is supplied. The inflation liquid can, however, contain also a medicine, which serves for wound treatment and improves wound healing.

The inflation liquid is discharged into the body lumen preferably directly, once a proper liquid-proof connection between the head section of the anastomotic device and the body tissues surrounding the head section is established. With the formation of an intestinal anastomosis, the supply and/or delivery of the inflation liquid can take place, once the head section of the anastomotic device has passed the sphincter muscle. Thus an inadvertent discharge of the inflation liquid during further insertion of the anastomotic device into the body lumen is prevented.

While inserting the head section and/or when pushing the introducer sheath forward in the body lumen the retaining pin is not completely retracted and is found in a position, in which the retaining pin does not rise above the head section in axial direction and/or does not protrude over the front edge of the head section. Thus, an injury to the surrounding tissue can be avoided by the retaining pin. During insertion through the head section and/or when pushing the introducer sheath forward, the retaining pin is completely retracted into the head section. In the completely retracted condition the tip of the retaining pin is fully lowered in a channel in the head section and/or accommodated by the channel, the tip of the retaining pin in completely retracted condition reaches a maximum insertion depth. Accordingly the fluidic connection can be preferably configured for a discharge of the inflation liquid into the body lumen with essentially fully retracted retaining pin. In principle, the retaining pin can be slightly retracted, if there is an addition of the inflation liquid. It is essential that an addition of the inflation liquid is possible if a tip of the retaining pin does not protrude over the head section in axial (distal) direction.

The discharge of the inflation liquid into the body lumen can preferably take place at the distal face of the head section, so that in a simple way it is guaranteed that a liquid discharge is not possibly impaired by the surrounding body tissues lying close to the lateral surface and/or side of the head section.

With a preferred embodiment, the extendable and retractable retaining pin is led within the guide lumen that is concentrically arranged to the head section, whereby the inflation liquid can be supplied via an inlet and an outlet of the guide lumen. The guide lumen is connected with the fluid supply channel or forms a part of it. Inlet and outlet of the lumen form the fluid outlet. A fluid addition can be made then with the retracted pin laterally at the pin via an annular gap between the pin and a side panel of the head section restricting the lumen, for example a sleeve or the like. Thus, a uniform liquid discharge is design-wise possible in a simple way in the middle area of the face of the head section, which facilitates inflating of the surrounding body tissue. Further a relatively large flow rate of the inflation liquid can be discharged via the channel of the retaining pin, which renders possible a certain volume increase of the lumen within a short time.

In the case of another embodiment of the anastomotic device it may be provided that the head section has a distal hollow-cylindrical head, which includes a clamping mechanism, whereby the fluid outlet is provided in a circular distal front surface of the head section. With this embodiment, the inflation liquid is delivered through the hollow-cylindrical head section as such, preferably through clamping outlets in the front surface of the head section, through which even clamps are ejected on the thrust bearing part. With this embodiment, the clamping outlets must be connected with at least one fluid supply channel, in order to make the fluid supply possible from the outside through the introducer sheath.

The said anastomotic device can have a circular knife arranged concentric to the head section. Here it is possible that the inflation liquid can be delivered through the annular space between the knife and lateral panel of the head section restricting a middle lumen for extending and retracting the retaining pin. The side panel can be formed by a distal sleeve in the head section, wherein the retaining pin is guided while retracting from and extending in the sleeve. At least one fluid outlet is arranged in the area of the annular space at the distal face of the head section between the knife and the sleeve. Preferably a multiplicity of outlets are provided, which are arranged uniformly spaced from one another in circumferential direction. The inflation liquid is delivered thus evenly distributed over the periphery of the annular space, which leads to a uniform volume increase during inflating.

A further alternative embodiment can provide that the inflation liquid is delivered directly via the retaining pin. For this purpose, the retaining pin has at least one outlet for the inflation liquid and a channel for guiding the liquid, which is connected with the fluid supply channel or is a part of it. At least one outlet in the retaining pin can be configured and aligned in such a manner that the inflation liquid essentially exits the retaining pin arranged distal and/or coaxial to the head section, which simplifies the delivery of the inflation liquid into the body lumen. The retaining pin can have, for example, a multiplicity of radially arranged fluid outlets, wherein via each outlet a directed liquid discharge can be possible in front and/or in distal direction.

By collapsing the lumen it can happen that the body tissue from outside lies close to an outside peripheral area of the head section and thus a liquid delivery across the periphery and/or side of the head section is rendered more difficult. With a suitable arrangement and size of the fluid outlets, laterally at the head section it is possible in principle that the inflation liquid is delivered across the lateral surface of the head section into the body lumen. The head section can have preferably a maximum diameter at the distal end, wherein the fluid outlets are preferably located in the area of the distal end of the head section, further in the area of a distal edge section, which extends over a third of the overall length of the head section and has a width of less than 2 cm, in particular less than 1 cm. Outlets can be uniformly distributed over the extent and/or are provided circumferentially in the lateral surface. The delivery of liquid can take place preferably forwards and/or directed distal. In this way, a simple liquid supply and/or discharge can be ensured, if the surrounding body tissue lies close to the external surface of the head section when inserting the anastomotic device.

The fluid supply channel can be led out of the actuating part and if required, connected to a liquid reservoir for inflation liquid. For example, the fluid supply channel can be configured as hose or with a hose, wherein the hose can jut out for example 3 to 4 cm from the actuating part. In a simple way, this facilitates connection of a filling syringe with the inflation liquid to the hose. The hose can have a screw-type cap at its open end, in particular a three-way connection, which allows the addition of different fluids on the one hand and/or the liquid-proof seal, on the other hand. The hose can be retracted laterally from the actuating part, which facilitates a connection to a reservoir. Further, the invention allows that a reservoir for inflation liquid is firmly connected with the actuating part and/or forms a part of the same. The anastomotic device has then a container or the like, which is filled with the inflation liquid. While inflating, the inflation liquid is withdrawn from the container via the fluid supply channel into the body lumen. Finally an equivalent embodiment can provide a fluid supply from outside via the introducer sheath and the head section, whereby the fluid can be supplied to the anastomotic device in an area, which lies between the head section and the actuating part of the said anastomotic device.

Further features of the invention are described in the claims, in the description of the figures as well as in the figures themselves, whereby all individual characteristics and all characteristic combinations are contemplated, even if the latter is not described in detail.

In the following, embodiments of the invention are described as examples and referring to the figures, wherein the invention is not limited to the embodiments as shown in the figures and wherein the characteristics of the embodiments can be combined with one another, without having to describe this is in detail. In particular, the subsequently described alternative possibilities of delivering the inflation liquid via the head section of the anastomotic device into the body lumen can be combined with one another.

BRIEF DESCRIPTION OF THE DRAWINGS

Embodiments of the presently disclosed anastomotic device are described herein with reference to the accompanying drawings, wherein.

DETAILED DESCRIPTION

Figure 1:
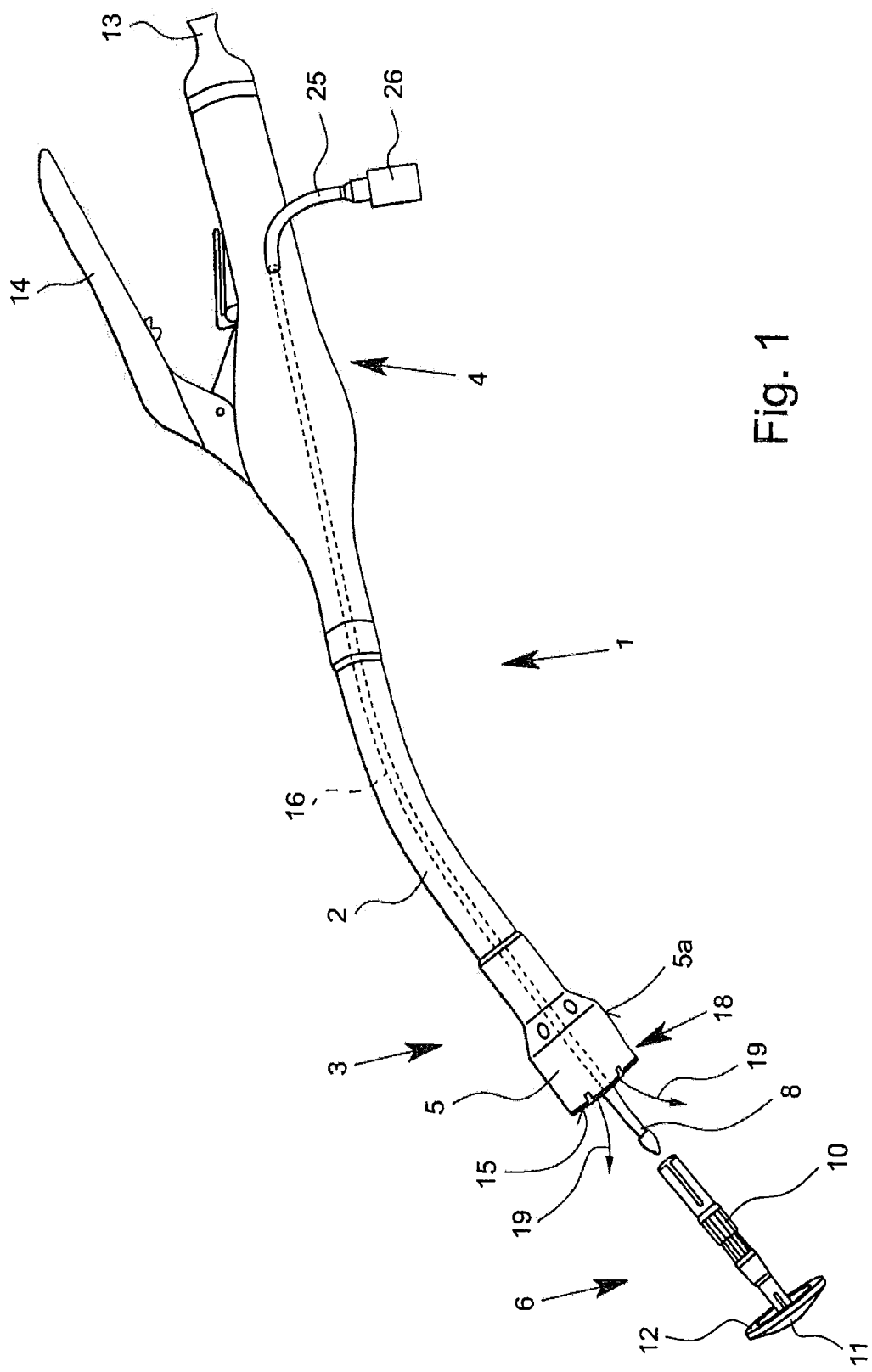
FIG. 1 a perspective view of the said anastomotic device designed for implanting a surgical staple inserter for anastomoses.

The disclosure relates to anastomotic device for the formation of anastomoses, in particular intestinal anastomoses, with an introducer sheath for feeding into a body lumen, preferably into the large intestine, with a particularly thickened or swelled head section at the distal end of the introducer sheath and with an actuating part at the proximal end of the introducer sheath. The anastomotic device has an anvil section with a thrust bearing part, and a retractable and extendable knife and a retaining pin arranged within the head section. The thrust bearing part can be moved relative to the head section. The retaining pin can be joined to the thrust bearing part of the anvil section. The thrust bearing part can be moved by moving the retaining pin into the head section. From the viewpoint of invention, the expressions "proximal" and "distal" refer to the field of vision of the person operating the anastomotic device, i.e. "proximal" on the person with respect to the side turned toward the person operating the anastomotic device and "distal" to the side away from the person FIG. 1 shows an anastomotic device 1 for forming anastomoses, in particular intestinal anastomoses, with an introducer sheath 2 for inserting into a tubular body lumen (not shown here), for example into a proximal portion of the large intestine through the anus, with a head section 3 at the distal end of the introducer sheath 2 and with an actuating part 4 at the proximal end of the introducer sheath 2. The head section 3 has a distal hollow-cylindrical head section 5, which houses the clamping mechanism (not shown in detail). When clamping by means of the anastomotic device 1, the fasteners or clamps (not shown) of the head section 3 can be moved to a thrust bearing part and/or anvil section 6. Within the head section 3, a ring-shaped extendable and retractable knife 7 and a retaining pin 8 are arranged, wherein the retaining pin 8 can be extended and retracted into the head section 3. The knife 7 and the retaining pin 8 are arranged concentric to the hollow-cylindrical head section 5, wherein the retaining pin 8 is arranged centrically in the head section 3. In the case of the retaining pin 8 that can be extended from the head section 3, as is shown in FIG. 1, the latter can be connected with a shaft or vertical passageway 10 of the thrust bearing part 6, wherein the shaft 10 is connected with anvil 11. On the proximal side and/or the side facing the head section 3, anvil 11 has a circular anvil surface 12 with clamp shaping recesses (not shown). The connection of retaining pin 8 and thrust bearing part 6 can take place by snapping in the retaining pin 8 and the shaft 10.

The retaining pin 8 is extended and retracted by turning a flattened adjusting screw 13 at the proximal end of the actuating part 4. The clamping mechanism is actuated by means of an operating grip 14 of the actuating part 4, wherein during operation of the operating grip 14 in a sequence matching the operation procedure knife 7 is also extended.

For producing an intestinal anastomosis, the anastomotic device 1, as shown in FIG. 1, can be used as follows. After removing a diseased part of the large intestine, it is necessary to produce the continence to join the remaining proximal portion and the distal portion of the large intestine through a suture. For this purpose, the thrust bearing part 6 is sewn into the proximal portion of the large intestine. This portion of the large intestine surrounds the anvil 11, while the shaft 10 juts out from this portion of the large intestine. Subsequently, the anastomotic device 1 is inserted with a fully retracted retaining pin 8 through the anus and pushed forward up to the distal portion of the intestine sealed with a cross suture. Then the retaining pin 8 is shifted to the maximum extended position in accordance with FIG. 1 and punctures the suture in the distal portion of the intestine.

After connecting the retaining pin 8 with the shaft 10 of the thrust bearing part 6, the thrust bearing part 6 is moved by inserting the retaining pin 8 into the head section 3 against the head section 3, until the intestine ends lie close together. The clamping mechanism is then activated, wherein the clamps are extended from a circular front surface 15 of the head section 5 and are moved against the facing circular anvil surface 12 and are bent there, so that the two intestinal parts or sections of tissue are interconnected. During actuation of the clamping mechanism by means of the operating grip 14, knife 7 is extended from the head section 3, so as to separate a tissue part, which is located within the periphery of the tissue clasped between the head section 3 and the thrust bearing part 6. According to the described clamping of the intestine parts, the anastomotic device 1 can be retracted from the body through the anal canal. DE application no. 10 2007 057 207 A1 discloses a method with the features as described before and a clamp inserter.

Deviating from the clamp inserter as known from DE 10 2007 057 207 A1, the anastomotic device 1, as shown in FIG. 1, is provided for the purpose of delivering an inflation liquid 19 via a fluidic, i.e. liquid-containing, connection between the actuating part 4 and the head section 3 into the body lumen and thus, effect an inflation of the (collapsed) body tissue. Filling the body lumen with the inflation liquid causes a volume increase, which facilitates a friction-free and an injury-free insertion of the anastomotic device into the body lumen, for example through the anal canal into the distal portion of the large intestine. Also for a leak test of a suture, which seals, for example, the distal portion of the intestine, inflating the body lumen before producing the anastomosis is of advantage. Supply of a coloured inflation liquid allows a visual control during insertion of the anastomotic device 1 and during the leak test of the suture in a simple manner, wherein it is determined whether and to what extent a liquid has penetrated the suture.

In the case of anastomotic device 1 as shown in FIG. 1, there is an inter-connected fluid supply channel 16 extending to the head section 3 and at least one fluid outlet connected with the fluid supply channel 16 (not shown in FIG. 1). The configuration of the fluidic connection allows thereby a liquid discharge via the anastomotic device during insertion in the head section 3 into the body lumen, for example with an intestinal anastomosis once a distal boundary region 18 of the head section 3 has passed the sphincter muscle, and/or when pushing the introducer sheath 2 forward.

As per FIG. 1, the inflation liquid 19 can also be delivered if the retaining pin 8 is extended at least area-wise out of the head section 3 and/or a tip of the retaining pin 8 juts out across the distal outer edge of the head section 3. Because the retaining pin 8 during insertion of the anastomotic device into the body lumen is usually fully retracted into the head section 3, the fluidic connection is configured for the delivery of the inflation liquid into the body lumen even in the case of partly, preferably complete, retracted retaining pin 8. In the retracted condition, the tip of the retaining pin 8 is arranged inside the head section 3. With completely retracted retaining pin 8, a maximum insertion depth of the retaining pin 8 is reached.

The delivery of the inflation liquid 19 into the body lumen via the distal face 19 of the head section 3 is advantageous, since in this area a largely unhindered liquid discharge is possible also in a collapsed body lumen.

Figure 2:
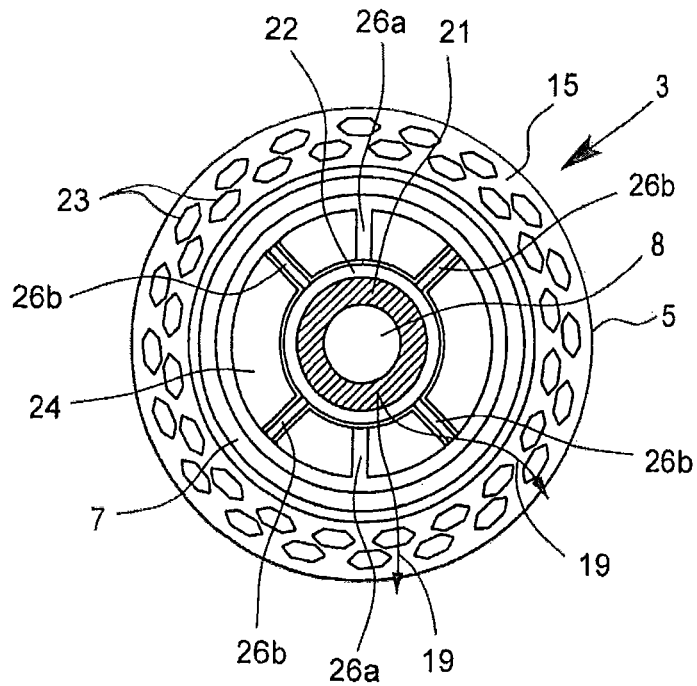
FIG. 2 a distal front view of a head section of the said anastomotic device with a first embodiment of the invention.

As can be seen from FIG. 2, the retaining pin 8 can be led in an extendable and retractable manner within guide lumen 21 arranged concentric to the head section 3. The guide lumen 21 has an inlet and an outlet for inflation liquid 19. The inflation liquid 19 is delivered through the guide lumen 21, wherein the guide lumen 21 in radial direction is surrounded by a sleeve 22. The sleeve 22 is arranged stationary in the head section 3 and is flexibly guided into the retaining pin 8.

Figure 3:
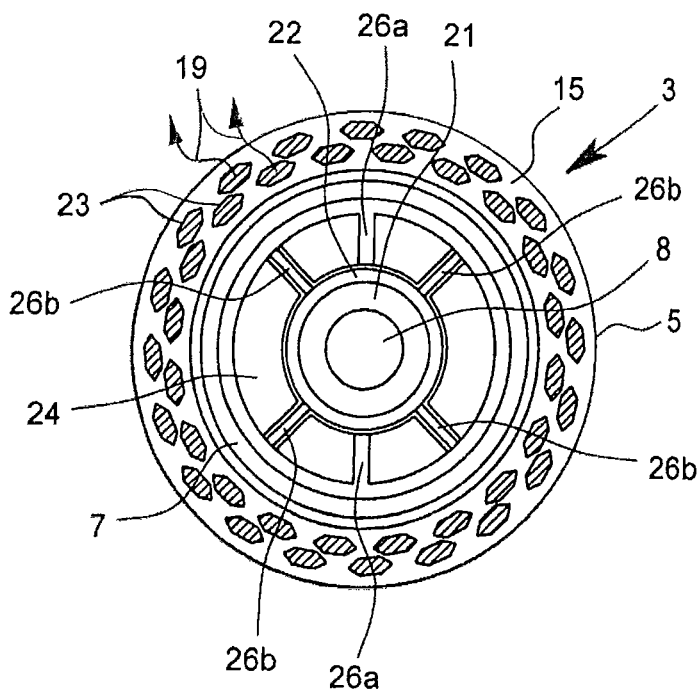
FIG. 3 a distal front view of a head section of the said anastomotic device with a second embodiment.

In the case of an alternative embodiment of the anastomotic device 1 as shown in FIG. 1, as shown in FIG. 3, the inflation liquid is delivered through the clamp outlets 23 of the clamping mechanism in a circular front surface 15 of the head section 5. In principle, further outlets (not shown) may be provided in the front surface 15, so that the liquid delivery does not take place via the clamp outlets 23.

Figure 4:
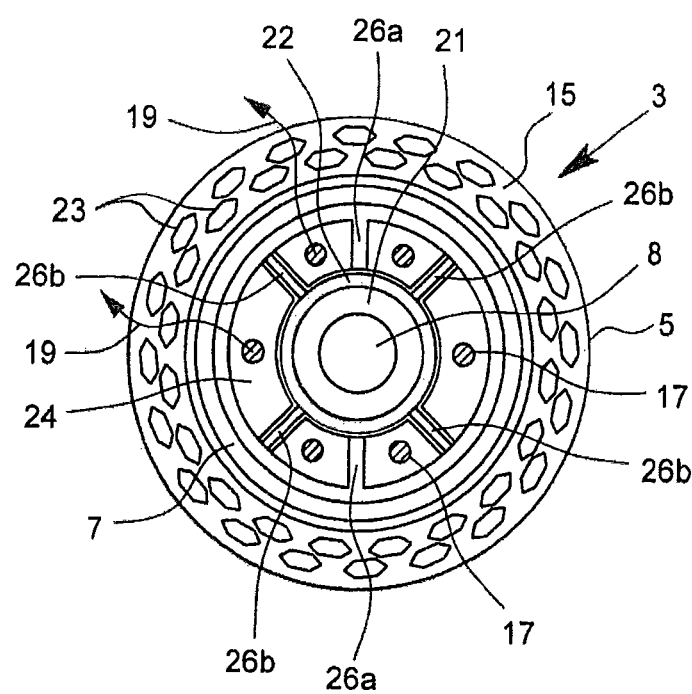
FIG. 4 a distal front view of a head section of the said anastomotic device with a third embodiment.

In the case of the embodiment of the anastomotic device 1, as shown in FIG. 4, the inflation liquid 19 is delivered via the annular space between the knife 7 and the sleeve 22. A Knife 7 is firmly connected with a pusher part 24 and flexibly arranged together with the pusher part 24 relative to the sleeve 22. That pusher part 24 has two guide webs 26a and recesses for further guide webs 26b fixed stationary at the sleeve 22, so that a guided movement of pusher part 24 together with the knife 7 is possible in axial direction. In the area between the webs or bars 26a and the recesses for the stationary webs 26b, the pusher part 24 has conical side panel sections extending toward the actuating part 4 in an axial direction. The liquid supply can be made now through the fluid outlets 17 in the side panel sections of pusher part 24. Alternatively and/or additionally, the inflation liquid is delivered through gap spaces between side panel sections of pusher part 24 and the sleeve 22 and/or the further guide webs 26b.

Although not shown in detail, the head section 3 can have a distal lateral surface 5a, in the distal boundary region 18, with at least one fluid outlet, and preferably a multiplicity of fluid outlets evenly distributed in a circumferential direction, arranged to deliver inflation liquid via the distal lateral surface 5a outlet or outlets.

As can be finally seen from FIG. 1, a hose 25 may be provided on a side of the actuating part 4, and the hose can be connected with the fluid supply channel and/or forms the fluid supply channel 16. The hose 25 can be connected to a reservoir for inflation liquid 19 (not shown). For the sake of simplicity, the hose 25 has a free end with a screw-type cap 26. The screw-type cap 26 can be unscrewed in a simple and a filling syringe or the like is used to introduce the inflation liquid 19 via the hose 25 and the fluid supply channel 16 to the head section 3. Although not shown, a three-way connection may be provided, which in a simple way facilitates the supply of different liquids via hose 25 and the fluid supply channel 16.

It is envisioned that between about 0.60 oz and about 17.0 oz of inflation liquid 19 is discharged through the fluid outlet(s). In embodiments, between about 1.0 oz and about 11.0 oz of inflation liquid 19 is discharged through the fluid outlet(s). It is further envisioned that the amount of inflation liquid 19 that is used is at least partially determined by the bursting pressure of the hollow tissue organ (e.g., within or adjacent a rectal stump) near the staple line, such that the amount of inflation liquid 19 used does not cause the pressure in the hollow tissue organ near the staple line to exceed the bursting pressure. The use of a pressure sensor or other conventional methods can be used to determine the actual pressure.

It is further envisioned that inflation liquid 19 is discharged through the fluid outlet(s) at a rate of between about 0.01 oz/s and about 0.70 oz/s. In embodiments, inflation liquid 19 is discharged through the fluid outlet(s) at a rate of between about 0.03 oz/s and about 0.34 oz/s.

It is further envisioned that anastomotic device 1 is inserted into and/or retracted from the body lumen at a rate of between about 0.03 in/s and about 4.0 in/s. In embodiments, anastomotic device 1 is inserted into and/or retracted from the body lumen at a rate of between about 0.10 in/s and about 2.0 in/s.

What is claimed is:

1. An anastomotic device comprising:
  a head section including:
    an annular housing including a plurality of staples therein;
    an annular guide lumen including inner and outer walls defining an annular channel therebetween, the outer wall spaced apart from the annular housing;
    a retaining pin movable within the annular guide lumen;
    a sleeve disposed about the annular guide lumen and stationary within the annular housing; and
    an annular knife disposed about the sleeve; and
  a fluid supply in fluid communication with the annular guide lumen to supply a fluid out of the annular housing.

2. The anastomotic device according to claim 1, further including an anvil section movable relative to the head section.

3. The anastomotic device according to claim 2, wherein the anvil section includes a shaft coupled with the retaining pin for concomitant displacement therewith.

4. The anastomotic device according to claim 1, wherein the fluid supply is in fluid communication with the annular guide lumen when the retaining pin is in a retracted position.

5. The anastomotic device according to claim 1, wherein the annular guide lumen defines a continuous annular space.

6. An anastomotic device comprising:
  a head section including:
    an annular housing including a plurality of staples therein;
    an annular guide lumen including inner and outer walls defining an annular channel therebetween, the outer wall spaced apart from the annular housing;
    a retaining pin movable within the annular guide lumen;
    a sleeve disposed about the annular guide lumen and stationary within the annular housing;
    an annular knife concentrically arranged with the sleeve; and
    a pusher part connected to the annular knife such that the pusher part and the annular knife are movable as a single construct, the pusher part disposed radially outward of the sleeve; and
  a fluid supply in fluid communication with the pusher part to supply a fluid out of the head section.

7. The anastomotic device according to claim 6, wherein the annular guide lumen is concentrically arranged with the annular housing.

8. The anastomotic device according to claim 6, wherein the sleeve includes a guide web extending radially outward therefrom.

9. The anastomotic device according to claim 8, wherein the pusher part defines a recess configured to receive the guide web of the sleeve therethrough.

10. The anastomotic device according to claim 6, wherein the pusher part includes an outlet at a distal surface thereof to discharge the fluid through the outlet.

11. The anastomotic device according to claim 6, wherein the pusher part is disposed about the sleeve.

12. The anastomotic device according to claim 6, further including an anvil section coupled to the retaining pin such that the anvil section is movable relative to the head section.

13. The anastomotic device according to claim 6, the pusher part includes a plurality of outlets circumferentially arranged about the sleeve.

14. The anastomotic device according to claim 6, wherein the annular guide lumen defines a continuous annular space.

15. The anastomotic device according to claim 6, wherein the annular knife is disposed radially outward of the sleeve.

16. The anastomotic device according to claim 6, wherein the pusher part is flexibly arranged with the sleeve.

\* \* \* \* \*